United States Patent [19]

Idemoto et al.

[11] Patent Number: 5,058,570
[45] Date of Patent: Oct. 22, 1991

[54] ULTRASONIC SURGICAL APPARATUS

[75] Inventors: Morito Idemoto; Yasuo Noguchi, both of Yokohama, Japan

[73] Assignee: Sumitomo Bakelite Company Limited, Tokyo, Japan

[21] Appl. No.: 245,401

[22] PCT Filed: Nov. 27, 1986

[86] PCT No.: PCT/JP86/00606
§ 371 Date: Jul. 21, 1988
§ 102(e) Date: Jul. 21, 1988

[87] PCT Pub. No.: WO88/03783
PCT Pub. Date: Jun. 2, 1988

[51] Int. Cl.$^5$ ............................................. A61B 17/22
[52] U.S. Cl. ................................ 128/24 AA; 606/128; 604/22
[58] Field of Search ............ 128/328, 24 AA; 604/22; 606/15, 128

[56] References Cited

U.S. PATENT DOCUMENTS

| | | |
|---|---|---|
| 2,227,727 | 1/1941 | Leggiadro . |
| 3,433,226 | 3/1969 | Boyd . |
| 3,543,757 | 12/1970 | Balaev . |
| 3,556,079 | 4/1971 | Ozimo ................. 128/24 A |
| 3,565,062 | 2/1971 | Kuris .................. 128/24 A |
| 3,792,701 | 2/1974 | Kloz et al. ............. 128/7 |
| 3,823,717 | 7/1974 | Pohlman et al. . |
| 3,830,240 | 8/1974 | Antonevich et al. . |
| 3,896,811 | 7/1975 | Storz . |
| 3,927,675 | 12/1975 | Pohlman et al. ........ 128/328 |
| 4,160,450 | 7/1979 | Doherty ............... 604/164 |
| 4,517,977 | 5/1985 | Frost ................. 604/22 |
| 4,594,996 | 6/1986 | Ibrahim et al. ......... 128/328 |
| 4,867,141 | 9/1989 | Nakada et al. ......... 128/24 A |
| 4,870,953 | 10/1989 | DonMicheal et al. ..... 127/24 A |

FOREIGN PATENT DOCUMENTS

| | | |
|---|---|---|
| 6055408 | 9/1983 | Japan . |
| 6055409 | 9/1983 | Japan . |
| 60-116347 | 6/1985 | Japan . |
| 0198703 | 10/1986 | United Kingdom . |

Primary Examiner—Ruth S. Smith
Attorney, Agent, or Firm—Browdy and Neimark

[57] ABSTRACT

An ultrasonic surgical apparatus for crushing, sucking and removing undesirable substances inside the body such as an ulcerous tissue, thrombus and calcium clod by means of mechanical vibrations of a flexible ultrasonic probe (17). The surgical apparatus comprises a horn (5) connected to an ultrasonic vibration source (4) and adapted to transmit and amplify mechanical vibrations of an ultrasonic frequency, an ultrasonic probe (17) including a flexible linear transmitting member (44) having a working portion (21) adapted to effect mechanical vibration of an ultrasonic frequency, a horn cover (6) at least a portion of which is made of a flexible material, and a flexible tube (8) having three inner holes and three branch tubes communicating with the inner holes and connected to the horn cover (6) through the one branch tube (7). The ultrasonic probe (17) is disposed in one of the inner holes (20) communicated with the latter one branch tube (7), and a suction device (11) and a liquid injector (14) are connected to two of the branch tubes.

5 Claims, 3 Drawing Sheets 5,058,570

ULTRASONIC SURGICAL APPARATUS

TECHNICAL FIELD

The present invention relates to an ultrasonic surgical apparatus for crushing, sucking, and removing undesirable substances existing in the body, such as ulcerous tissue, thrombi, calcification aggregates, by means of ultrasonic vibrations of a flexible ultrasonic probe.

BACKGROUND ART

Conventionally, as the methods of removing thrombi, there is a method of inserting a catheter into a thrombus portion and dissolve the thrombus by injecting thereinto a thrombolytic agent such as streptokinase (e.g., Japanese Patent Unexamined Publication No. 57-173065); a method of withdrawing a catheter while maintaining the balloon of a balloon catheter in an expanded state and, at the same time, removing a thrombus (e.g., Japanese Patent Examined Publication No. 49-16472); and a method of clamping a thrombus portion by two expanded balloons, softening the thrombus by injecting a thrombolytic agent thereinto, and withdrawing a catheter and at the same time removing the thrombus (e.g., Published Japanese Translation of PCT Appln., Publication No. 58-501983).

However, even if the thrombolytic agent is injected locally through the catheter, there is a drawback in that the thrombolytic agent flows into normal terminal blood vessels and the like, thereby entailing the risk of hemorrhage in the terminal blood vessels and the like. Further, in the case where the catheter was withdrawn while maintaining the balloon of the balloon catheter in a expanded state to simultaneously remove the thrombus from the body, there was the risk of causing damage to the inner wall of a blood vessel since a safety measure against a tensile stress applied to the inner wall of the blood vessel has not been taken. In the case where a catheter provided with two balloons, was used as a similar method of removing a thrombus, when the catheter was to be used to clamp a thrombus 27 between two balloons 31, 32 (see FIG. 7), the balloon 32 located closer to the tip of a catheter 30 needed to be inserted from a position 34 in front of a thrombus 27 up to a position 35 which is deeper than that of the thrombus 27, so that there was the danger of pushing, by the balloon 32, the thrombus 27 in the inserting direction 33 as illustrated in FIG. 7, thereby moving the thrombus 27 to another part, such as a terminal blood vessel.

Furthermore, as a method of mechanically removing a thrombus, a drill bit is provided at the tip of a bar-like member, the drill bit being made to rotate by rotating the bar-like member, and the thrombus is crushed by the drill bit rotation. With this method, however, a torsional stress is applied to the inner wall of the blood vessel, so that there is a drawback in that the blood vessel may be cut off by the stress, and adjustment of the number of revolutions and the like is hence made difficult.

Further, a surgical apparatus using ultrasound has recently become known in which an ultrasonic probe connected to a source of ultrasonic vibration is used to crush tissue, a calcification aggregate, thrombus, or the like by mechanical vibrations of an ultrasonic frequency at the tip of the ultrasonic probe, and the crushed tissue, calcification aggregate, thrombus, or the like is removed through an inner hole provided in the ultrasonic probe (e.g., Japanese Patent Unexamined Publication Nos. 60-5139 and 49-21989). With such a device, however, since the ultrasonic probe having a working portion which mechanically vibrates at an ultrasonic frequency was not flexible, there was a drawback in that it would be difficult to insert it into a curved blood vessel or a tubular tissue inside the body.

SUMMARY OF THE INVENTION

The present invention is aimed at removing such drawbacks of the conventional methods of removing thrombi as the fear of hemorrhage caused by a thrombolytic agent, the risk of causing damage to blood vessel owing to a tensile or torsional stress applied to the inner wall of the blood vessel by the balloon catheter, or the movement of the thrombus, upon insertion of the balloon catheter, and is also aimed at enabling the crushing and removal of a thrombus, a calcification aggregate or the like in the tubular tissue of a curved blood vessel or the like for which an operation has previously been difficult to conduct with the conventional ultrasonic surgical device. As a result of the diligent study, there was completed an ultrasonic surgical apparatus which is capable of allowing a flexible ultrasonic probe to be inserted directly into the affected part, crushing an undesirable substances in the body such as a thrombus and a calcification aggregate by means of mechanical vibrations of an ultrasonic frequency, and removing the same by suction without affecting the normal surrounding tissue.

Namely, the present invention provides an ultrasonic surgical apparatus including an ultrasonic vibration source for generating ultrasonic vibrations, an oscillator for supplying high-frequency electric energy to the ultrasonic vibration source, a horn connected to the ultrasonic vibration source and adapted to transmit and amplify mechanical vibrations of an ultrasonic frequency, and a suction device for sucking and removing an undesirable substances from an operated part, characterized in that there are provided an ultrasonic probe which is constituted by a flexible elongated transmitting member, such as a flexible wire, secured at one end to a tip of the horn and having at the other end a working portion adapted to effect mechanical vibration of an ultrasonic frequency, a horn cover at least a portion of which is made of a flexible material, and a flexible tube having three inner holes and one or three branch tubes communicating with the inner holes and connected to the horn cover, and that the ultrasonic probe is disposed in the one inner hole and the suction device is connected to the one branch tube.

BRIEF DESCRIPTION OF DRAWINGS

FIGS. 3(a) and 3(b) are enlarged views of a bellows portion, in which FIG. 3(a) shows a state in which the bellows portion is expanded, while FIG. 3(b) shows a state in which the bellows portion is shrunk or compressed.

FIG. 8(a) is a view of the tip of the ultrasonic probe of the invention with an oblique-angled end.

FIG. 8(b) is a view of the tip of another embodiment of the ultrasonic probe of the invention with an arcuate end.

BEST MODE FOR CARRYING OUT THE INVENTION

Figure 1:
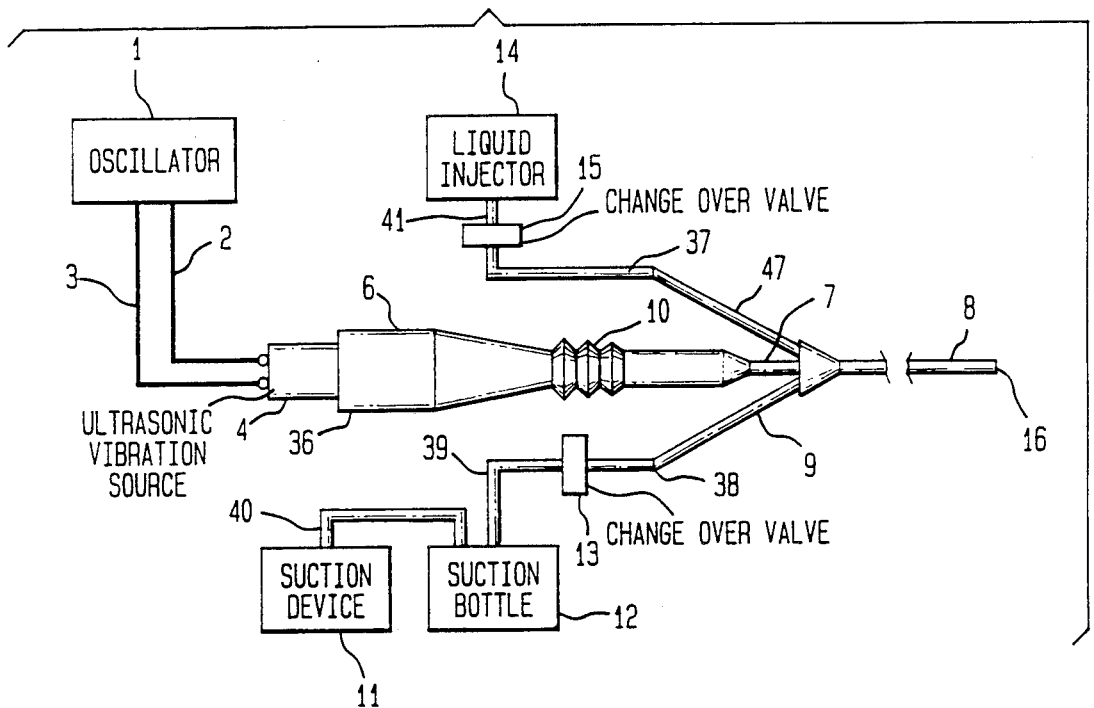
FIG. 1 is a view illustrating the overall construction of an ultrasonic surgical apparatus in accordance with an embodiment of the present invention.

Next, the invention will be described in detail with reference to the drawings. FIG. 1 is a view illustrating the overall construction of an ultrasonic surgical apparatus in accordance with an embodiment of the present invention. As shown in FIG. 1, the apparatus comprises four sections consisting of a section for generating mechanical vibrations of an ultrasonic frequency which is constituted by an oscillator 1 and a handpiece 36, a suction section constituted by a suction device 11 and a suction bottle 12, a liquid injecting section constituted by a liquid injector 14 for injecting an irrigation liquid, and a catheter section constituted by a flexible tube 8 and branch tubes 7, 9, and 47, the tube 7 having a bore 42.

Figure 2:
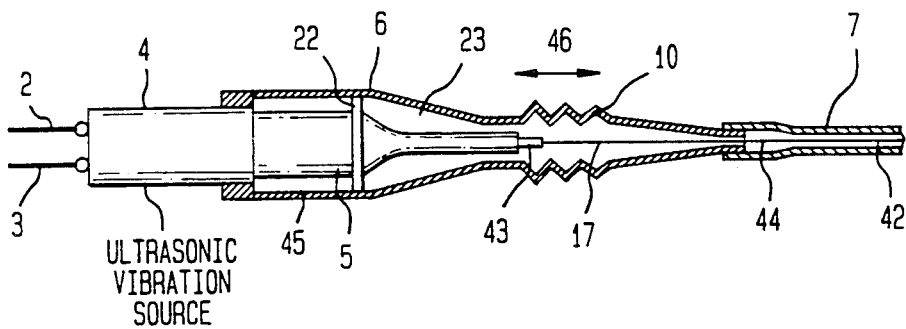
FIG. 2 is an enlarged diagram of a handpiece portion and illustrates the construction of the interior of a horn cover.

High-frequency electric energy is supplied from the oscillator 1 to the handpiece 36 via cables 2, 3. The handpiece 36 is, as shown in FIG. 2, constituted from an ultrasonic vibration source 4, a horn 5, a horn cover 6, and a flexible ultrasonic probe 17. The high-frequency electric energy is supplied to the ultrasonic vibration source 4, and the ultrasonic vibration source 4 generates mechanical vibrations of an ultrasonic frequency and the vibrations are transmitted to the horn 5. The mechanical vibrations are enlarged at the horn 5 and are transmitted to the ultrasonic probe 17.

The oscillator 1 has an oscillation circuit which is capable of supplying high-frequency electric energy corresponding to fluctuations in the state of the mechanical load of the horn 5 and the ultrasonic probe 17. Although 15-40 kHz is suitable as an oscillation frequency, 20-30 kHz is preferable in view of the mechanical vibrations of the ultrasonic frequency and the crushing capability of the ultrasonic probe 17.

Although the connection between the ultrasonic vibration source 4 and the horn 5 is made by a screwing method, it is not limited thereto. The ultrasonic vibration source 4 is not particularly restricted insofar as it converts high-frequency electric energy of the magnetostriction type, the electrostatic type, or the like into mechanical vibrations. As the material of the horn 5, a metallic material which is capable of transmitting and enlarging the mechanical vibrations of an ultrasonic frequency and has a fatigue strength sufficient to withstand the mechanic,,al vibrations is suitable, and stainless steel, duraluminum alloy, a titanium alloy, or the like is preferable.

Further, as a method of connecting the horn 5 and the ultrasonic probe 17, the screwing method, welding, or the like is suitable. The ultrasonic probe 17 is constituted by a fixing member 43 and a flexible elongated transmitting member 44, and, as a method of connecting the fixing member 43 and the elongated transmitting member 44, welding, adhesion, or the like is suitable. The materials of the fixing member 43 and the elongated transmitting member 44 are not particularly limited if they are capable of transmitting the mechanical vibrations of an ultrasonic frequency and have a fatigue strength capable of withstanding the mechanical vibrations. However, the materials through which an X-ray cannot be transmitted are preferable, and a metallic material such as stainless steel or a titanium alloy or a composite material such as carbon fiber-reinforced plastics is preferable. The horn cover 6 is provided around the horn 5 and the flexible ultrasonic probe 17. One end of the horn cover 6 is connected to the ultrasonic vibration source 4 by an appropriate method, while the other end thereof is connected to the branch tube 7 by means of an adhesive to retain airtightness. However, it is not limited to this connection method. The interior of the horn cover 6 is divided into partitioned chamber 23 and partitioned chamber 45 by means of a rubber O-ring 22, the rubber O-ring 22 being located at a node portion where the amplitude of the mechanical vibrations in the longitudinal direction 46 of the horn 5 is the minimum, and shielding the passage of the liquid. In addition, by providing a portion of the horn cover 6 with a bellows portion 10 formed of a flexible material, it is possible to move the branch tube 7 forth and back by virtue of the expansion and shrinkage of the bellows portion 10 in the longitudinal direction 46.

Figure 3A:
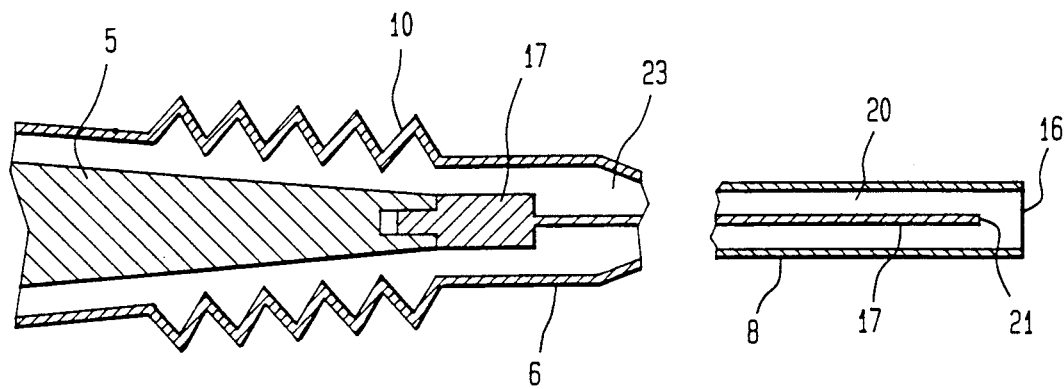

The ultrasonic probe 17 extends through the bore 42 of the branch tube 7, and is disposed inside the inner hole or bore 20 of the flexible tube 8 shown in FIG. 1. As shown in FIG. 3(a), the tip of the ultrasonic probe 17 has such a dimension that, when the bellows portion 10 is in an extended state, the tip will not protrude beyond the tip 16 of the flexible tube 8. By this structure, when the flexible tube 8 is inserted into the body, the tip of the ultrasonic probe 17 is located in the inner hole of the flexible tube 8, thereby making it possible to prevent a blood vessel or the like from being damaged by the tip of the ultrasonic probe 17.

Figure 4:
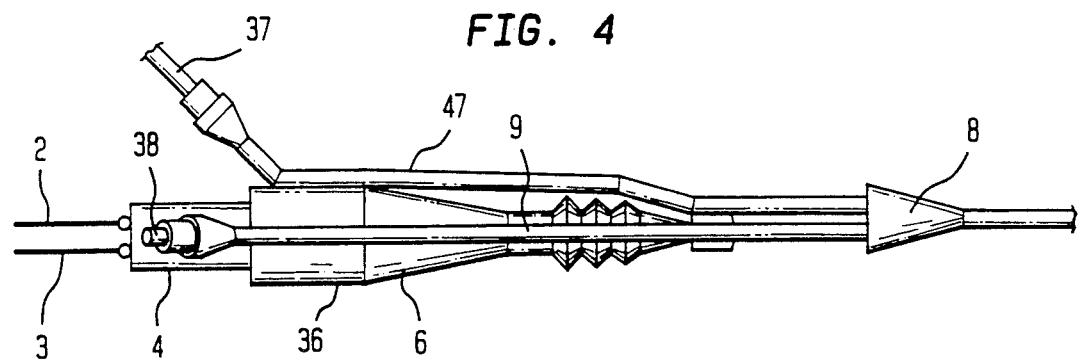
FIG. 4 is a view illustrating an example of the configuration of the handpiece.

Next, the suction device 11 is connected with the inner hole of the flexible tube 8 via the branch pipe 9, a changeover valve 13, the suction bottle 12, and tubes 38, 39, and 40, as shown in FIG. 1. Further, the liquid injector 14 is connected with the inner hole of the flexible tube 8 via the branch tube 47, a pipe 37, a changeover valve 15, and a tube 41. As a method of arranging the branch tubes 9 and 47, although FIG. 4 illustrates an example in which the branch tubes 9 and 47 are secured to the horn cover 6 by means of an appropriate adhesive, the arrangement of a configuration that facilitates the use by the operator is sufficient, not limited to the illustrated arrangement.

As for the method of using this apparatus, firstly, the partitioned chamber 23 and the inner holes or bores 42, 20 are filled with a liquid which is not harmful to the bodily tissue, such as physiological saline solution, by an appropriate means so as to facilitate slippage of the elongated transmitting member 44 installed inside the branch tube 7 and the flexible tube 8. For instance, a passage leading to the partitioned chamber 23 is provided on the side of the horn cover 6, a liquid such as physiological saline solution is injected into the partitioned chamber 23 and the inner holes 42, 20 through that passage, and the passage is then closed. Also, an inner suction hole 19 of the flexible tube 8 and the inner hole of the branch tube 9, communicating with the suction device 11, are filled with a liquid such as physiological saline solution by means of the operation of the suction device 11 and the changeover valve 13. With respect to the liquid injector as well, the branch tube 47 and the inner hole 20 are similarly filled with a liquid such as physiological saline solution.

Figure 3B:
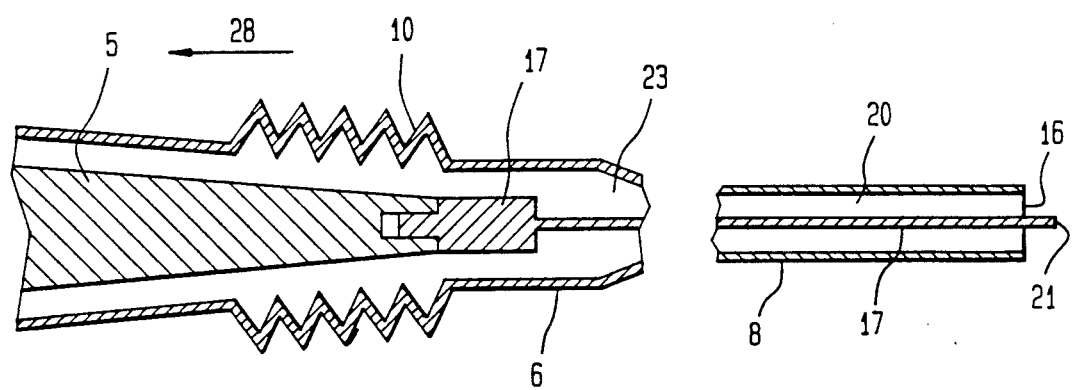
Figure 5A:
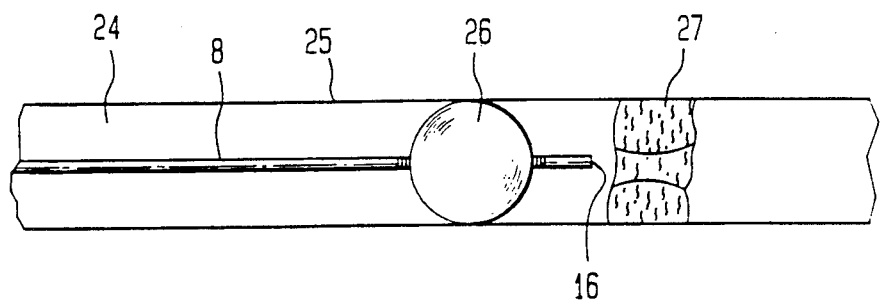
FIGS. 5(a) and 5(b) are views explaining an example of using the apparatus in accordance with the present invention.
Figure 5B:
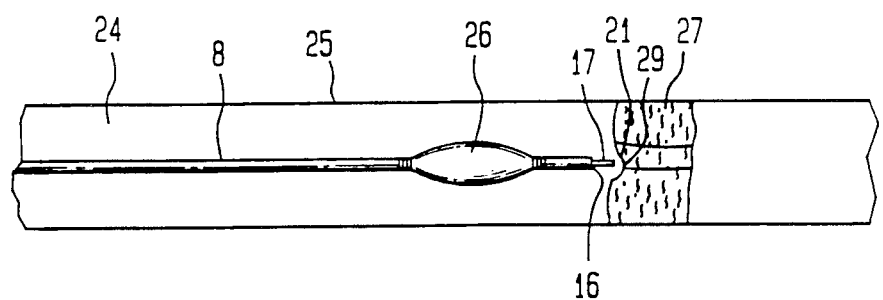

Next, while confirming the position of the tip of the elongated transmitting member 44 while projecting X-rays, the flexible tube 8 is inserted into the body and is inserted up to a portion to be operated on, e.g., a thrombus portion. For example, as shown in FIG. 5(a), a balloon 26 is provided in the vicinity of the tip 16 of the flexible tube 8. The balloon 26 is temporarily expanded using an inner hole (not illustrated, but similar to the inner hole 18 when the balloon is used) provided in the flexible tube 8 for the balloon to such an extent that it does not affect the flow of blood 24, so as to position the tip 16 since the flexible tube 8 sways owing to the flow of the blood inside a blood vessel 25. At this time, the mutual relationships between the flexible tube 8 and the elongated transmitting member 44 are in the state shown in FIG. 3(a). Subsequently, by shrinking or compressing the bellows portion 10 in the direction of the arrow 28 while holding a part of the horn cover 6 on the side of the branch tube 7 in relation to the bellows portion 10, a working portion 21 of the ultrasonic probe 17 is made to project from the tip 16 of the flexible tube 8, as shown in FIG. 3(b). Hence, the balloon 26 is deflated after adjusting the position in relation to the thrombus 27. Then, as shown in FIG. 5(b), the ultrasonic probe 17 is mechanically vibrated at an ultrasonic frequency, and the working portion 21 is brought into contact with the thrombus 27 to crush the thrombus 27. The small crushed pieces of the thrombus are sucked by the suction device 11 through the inner suction hole 19 shown in FIG. 6(a) and are removed out of the body. In addition, when the position of the thrombus 27 is unclear, a contrast medium or the like is injected through the liquidinjecting inner hole 18 shown in FIG. 6(a) by means of the liquid injector 14, and the above operation is carried out while confirming the position of the thrombus 27.

The material of the flexible tube 8 may be the some one which is normally used for a medical catheter, such as soft vinyl chloride resin. On the other hand, the materials of the branch tubes 7, 9, and 47 are not particularly limited, but one which is capable of adhering with the flexible tube 8 is preferable. The inner hole and outer periphery of the flexible tube 8 and the inner holes of the branch tubes 7, 9, 47 are coated with an antithrombotic substance. As this antithrombotic substance, polyurethane, hydrogel, heparinated polymer, urokinasecoupled polymer, or the like is preferable, but the substance is not particularly restricted.

Figure 6A:
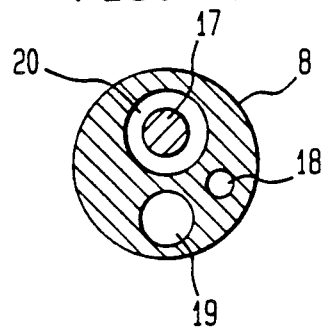
FIGS. 6(a) and 6(b) are views illustrating an example of the cross-sectional structure of a flexible tube.
Figure 6B:
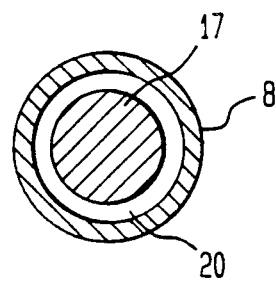
Figure 7:
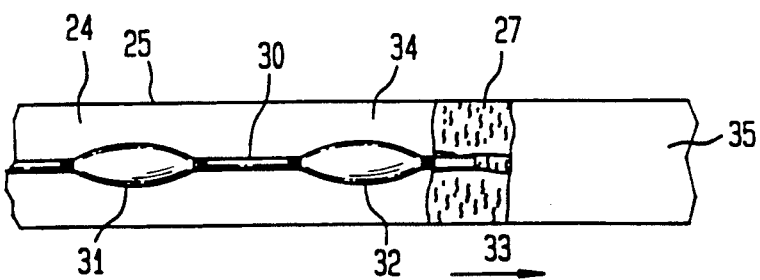
FIG. 7 is a view illustrating a conventional method.

Furthermore, while the construction of FIG. 6(a) is preferred, the number of the inner holes of the flexible tube 8 can be varied. For instance, even in the case where one inner hole 20 is provided as shown in FIG. 6(b), the inner hole 20 having the ultrasonic probe 17 can be used to make it communicate with the suction device 11 and the liquid injector 14 through a changeover valve.

An acute-angled portion is removed from the working portion 21 at the tip of the ultrasonic probe 17, so as to prevent damage of the inner wall of a blood vessel and the like. Although the configuration of an end surface thereof is not particularly restricted, an obliqueangled end 17a such as shown in FIG. 8(a) or an acute configuration 17b such as shown in FIG. 8(b) is preferred.

Although the description has been made in detail here with respect to the case where the apparatus is used for removal of a thrombus in a blood vessel as one embodiment according to the invention, the usage of the apparatus is not restricted to this and it goes without saying that the apparatus can be widely used for crushing and removing other undesirable substances in the body.

INDUSTRIAL APPLICABILITY

According to the present invention, it is possible to insert an ultrasonic probe directly into the affected part where an undesirable substance, such as a thrombus, calcification aggregate, ulcer, or the like occuring in a narrow tubular tissue such as a bent blood vessel is present, and crush the undesirable substance by means of mechanical vibrations of an ultrasonic frequency and immediately remove the same out of the body without adversely affecting the normal surrounding tissue. Further, an incised portion at the body surface can be made only slightly larger than the diameter of a flexible tube enveloping an ultrasonic probe. Hence, an operation which gives a very low level of stress to the patient can be carried out within a short period of time and the burden on the patient after the operation can be alleviated significantly, so that the apparatus is suitable as an ultrasonic surgical apparatus.

We claim:
1. In a ultrasonic surgical apparatus comprising an ultrasonic vibration source (4) for generating ultrasonic vibrations, an oscillator means (1) connected to said ultrasonic vibration source for supplying high-frequency electric energy to said ultrasonic vibration source, a horn (5) connected to said ultrasonic vibration source and adapted to transmit and amplify mechanical vibrations of an ultrasonic frequency, and a suction means (11) for sucking and removing an undesirable substance from an operated part, the improvement comprising,
   an ultrasonic probe (17) constituted by a flexible elongated transmitting member secured at one end to a tip of said horn and having at the other end a working portion adapted to effect mechanical vibration of said ultrasonic frequency,
   a horn cover (6) at least a portion of which is made of a flexible material,
   a flexible tube (8) having three inner nonconcentric, parallel, axially extending bores and three branch tubes each communicating with one of said inner bores, and connected to said horn cover,
   said ultrasonic probe extending through one of said inner bore and said suction means connected to one of said branch tubes,
   wherein a bellows-like portion of flexible material ia provided to a portion of said horn cover (6) to make said horn cover flexible.
2. An ultrasonic surgical apparatus according to claim 1, wherein said working portion (21) of said ultrasonic probe (17) is oblique-angled or arcuate in shape.
3. An ultrasonic surgical apparatus according to claim 1, wherein a liquid injector means (14) for injecting an irrigation liquid is in fluid connection with one of said branch tubes of said flexible tube (8).
4. An ultrasonic surgical apparatus according to claim 1, wherein said flexible tube (8) has an inflatable and deflatable balloon (26) adjacent said working portion of said ultrasonic probe (17).
5. An ultrasonic surgical apparatus according to claim 1, wherein the surface of said bore in which said ultrasonic probe (17) is disposed and outer periphery of said flexible tube (8) are coated with an antithrombotic substance.

* * * * *